(12) United States Patent
Park et al.

(10) Patent No.: US 8,072,226 B2
(45) Date of Patent: Dec. 6, 2011

(54) NANOSTRUCTURE SENSORS

(75) Inventors: Young June Park, Seoul (KR); Jun Ho Cheon, Seoul (KR); Sung Min Seo, Seoul (KR)

(73) Assignee: SNU R&DB Foundation (KR)

( * ) Notice: Subject to any disclaimer, the term of this patent is extended or adjusted under 35 U.S.C. 154(b) by 324 days.

(21) Appl. No.: 11/995,916

(22) PCT Filed: Aug. 6, 2007

(86) PCT No.: PCT/KR2007/003767
§ 371 (c)(1),
(2), (4) Date: Jul. 23, 2008

(87) PCT Pub. No.: WO2008/018726
PCT Pub. Date: Feb. 14, 2008

(65) Prior Publication Data
US 2010/0109645 A1    May 6, 2010

(30) Foreign Application Priority Data
Aug. 7, 2006  (KR) .................. 10-2006-0074322

(51) Int. Cl.
*G01R 31/02* (2006.01)
(52) U.S. Cl. ............................................. 324/537
(58) Field of Classification Search .............. 324/158.1, 324/537, 763, 765; 257/414, E27.01–E27.113
See application file for complete search history.

(56) References Cited

U.S. PATENT DOCUMENTS

| | | | |
|---|---|---|---|
| 6,918,284 B2 * | 7/2005 | Snow et al. .................. | 73/31.05 |
| 7,052,588 B2 | 5/2006 | Gu et al. | |
| 7,065,857 B2 | 6/2006 | Watanabe et al. | |
| 7,129,554 B2 * | 10/2006 | Lieber et al. .................. | 257/414 |
| 7,135,728 B2 * | 11/2006 | Duan et al. .................... | 257/296 |
| 7,233,041 B2 * | 6/2007 | Duan et al. .................... | 257/296 |
| 7,256,466 B2 * | 8/2007 | Lieber et al. .................. | 257/414 |
| 7,385,267 B2 * | 6/2008 | Lieber et al. .................. | 257/414 |
| 7,619,290 B2 * | 11/2009 | Lieber et al. .................. | 257/414 |
| 7,701,014 B2 * | 4/2010 | Mostarshed et al. .......... | 257/368 |
| 2004/0104129 A1 * | 6/2004 | Gu et al. ....................... | 205/775 |
| 2004/0192072 A1 | 9/2004 | Snow et al. | |
| 2006/0169585 A1 | 8/2006 | Nagahara et al. | |

(Continued)

FOREIGN PATENT DOCUMENTS
WO    WO2005074467       8/2005
WO    WO2006076044 A2   7/2006

OTHER PUBLICATIONS

Wolfgang Hoenlein et al.; "Nanoelectronics beyond silicon"; Microelectronic Engineering 83; pp. 619-623; 2006.

(Continued)

*Primary Examiner* — Huy Q Phan
*Assistant Examiner* — Joshua Benitez
(74) *Attorney, Agent, or Firm* — Fish & Richardson P.C.

(57) ABSTRACT

Embodiments feature a sensor including a nanostructure and methods for manufacturing the same. In some embodiments, a sensor includes a substrate, a first electrode disposed on the substrate, and a second electrode disposed on the substrate. The second electrode is spaced apart from the first electrode and surrounding the first electrode. The sensor includes at least one nanostructure contacting the first electrode and the second electrode, in which the nanostructure is configured to vary an electrical characteristic according to an object to be sensed.

46 Claims, 12 Drawing Sheets

U.S. PATENT DOCUMENTS

2010/0050745 A1* 3/2010 Liu et al. .................. 73/31.06
2010/0155696 A1* 6/2010 Duan et al. .................. 257/14

OTHER PUBLICATIONS

Michael W. Miller et al.; "Large-scale assembly of carbon nanotubes"; Nature Publishing Group; pp. 36-37; 2003.

International Search Report and Written Opinion of the ISA/KR for PCT/KR2007/003767; dated Nov. 14, 2007 (9 pages).

Extended European Search Report issued in 07807968.8 on Jan. 31, 2011, 7 pages.

Jing Li et al., "Carbon Nanotube Sensors for Gas and Organic Vapor Detection," Nano Letters, American Chemical Society, Washington, DC, vol. 3, No. 7, Jun. 13, 2003, pp. 929-933.

* cited by examiner

[Fig. 1]
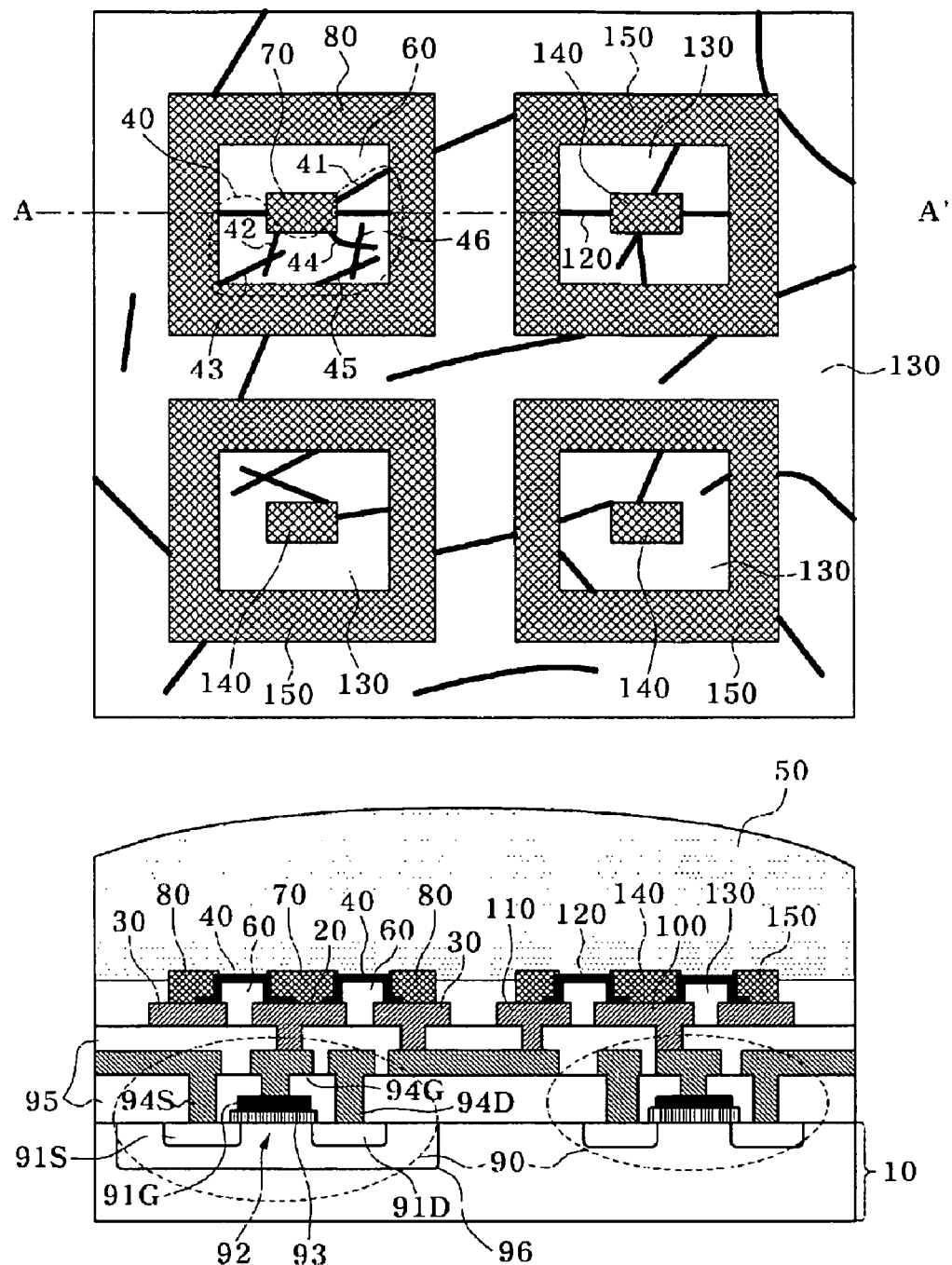

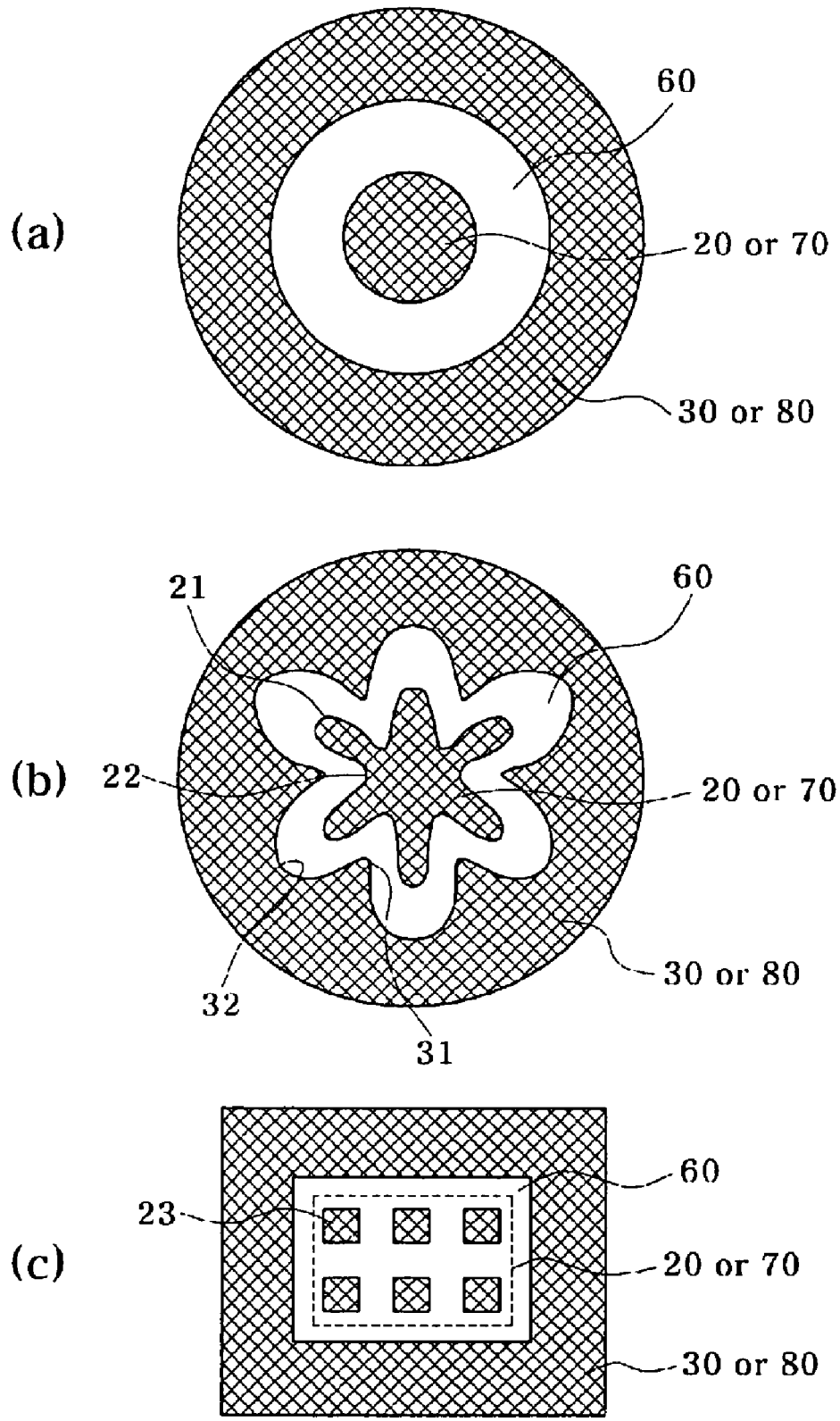
[Fig. 2]

[Fig. 3]
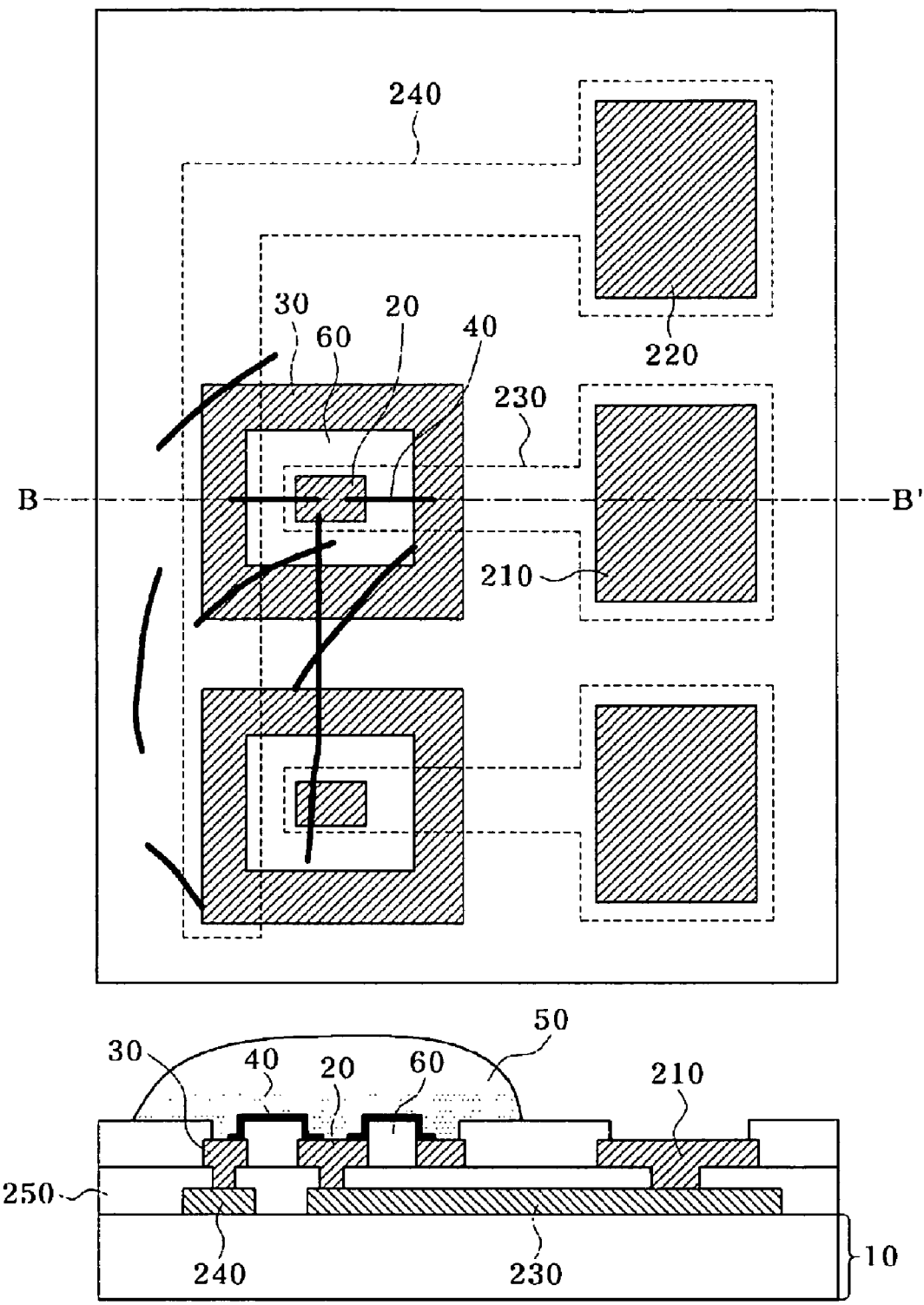

[Fig. 5]
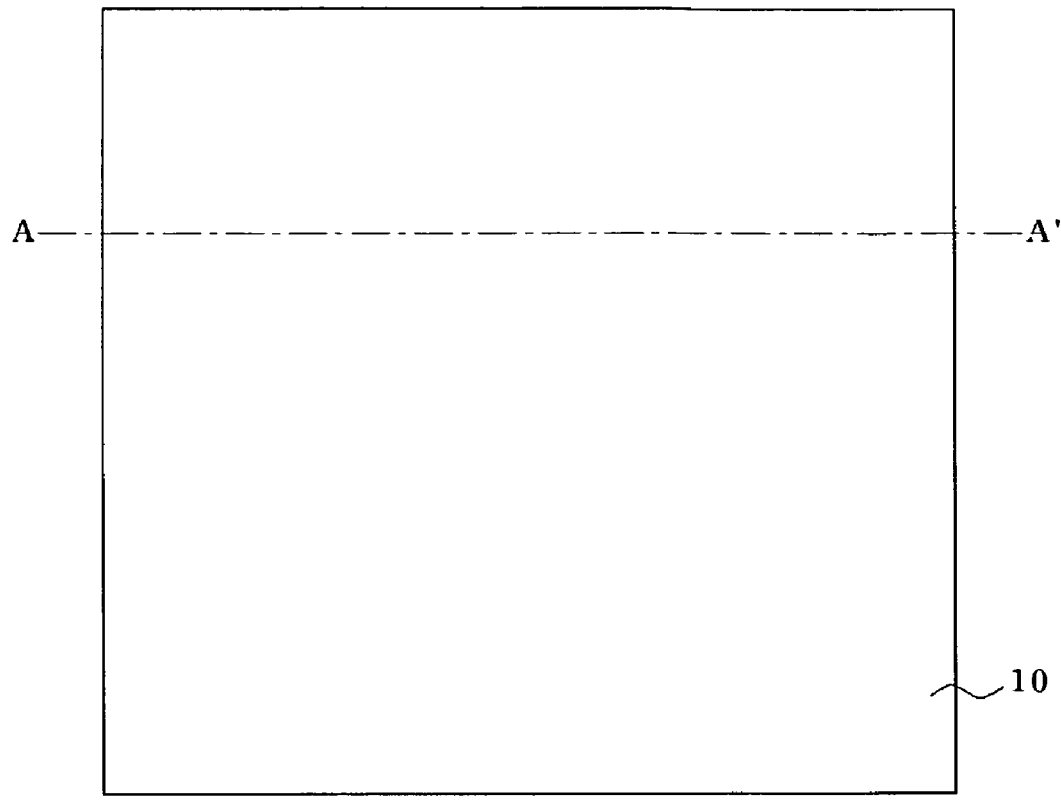
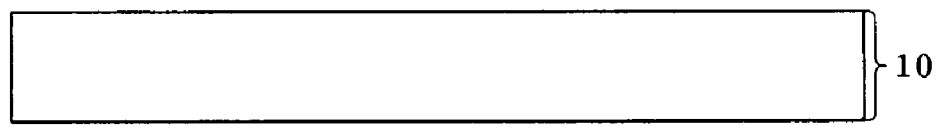

[Fig. 6]
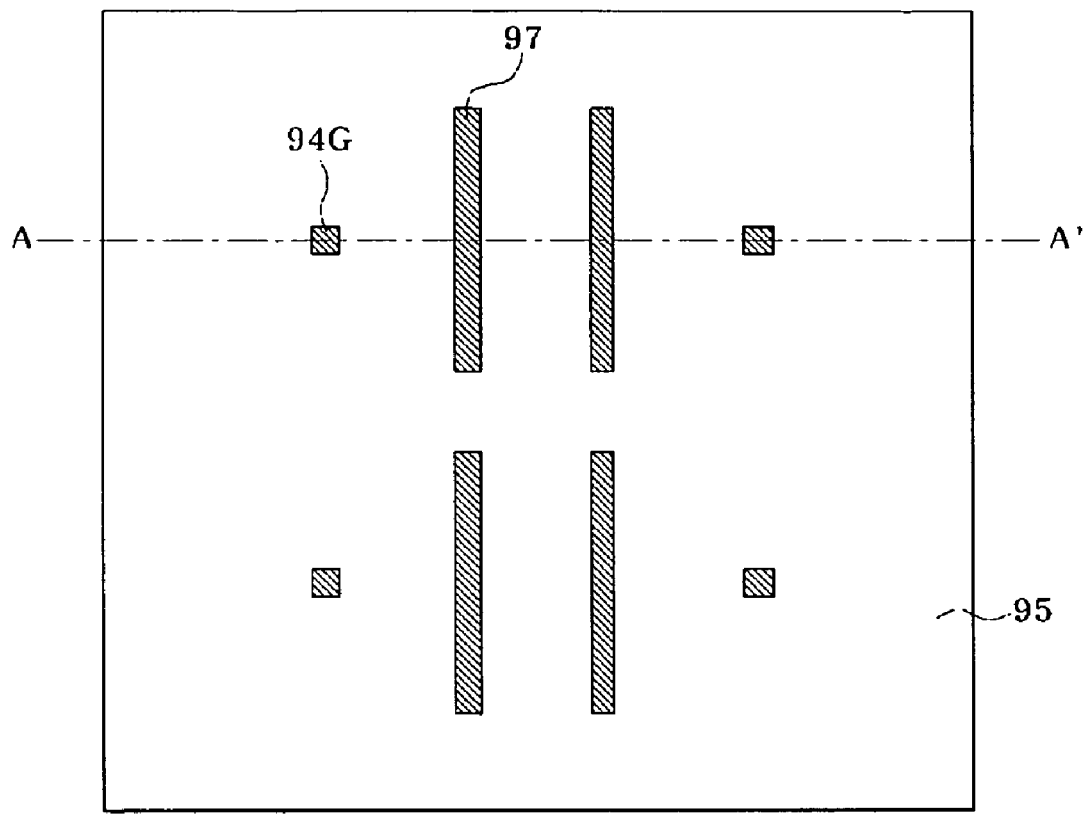
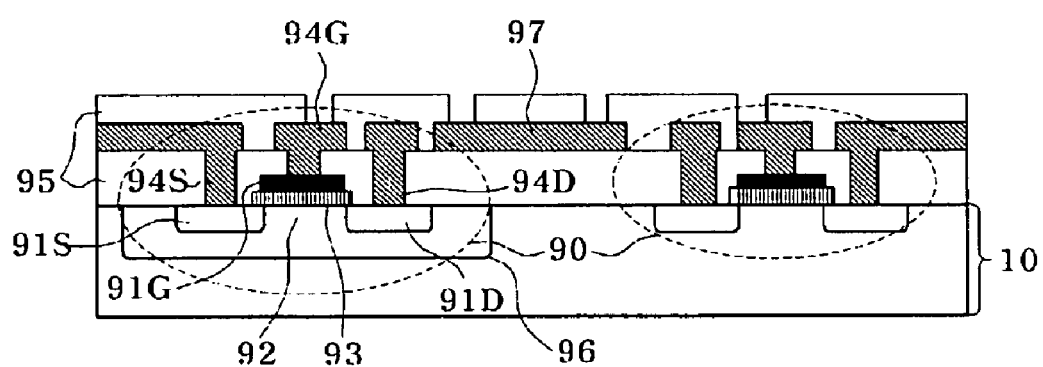

[Fig. 7]
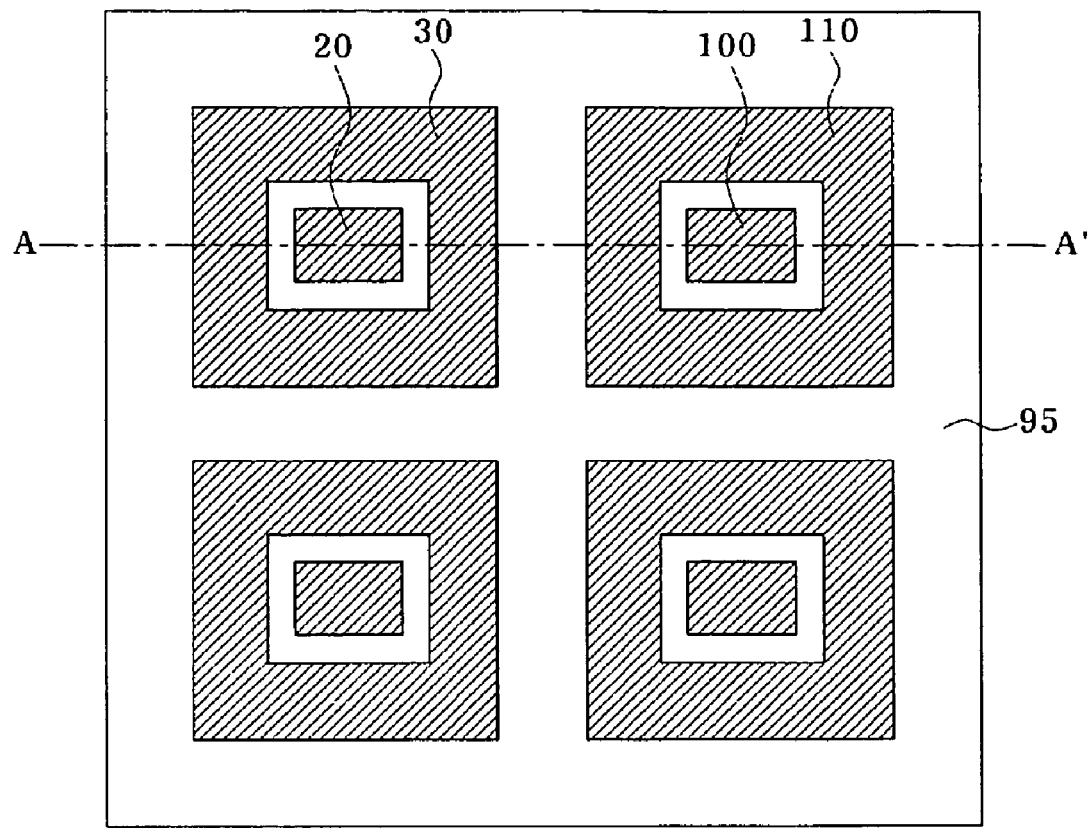
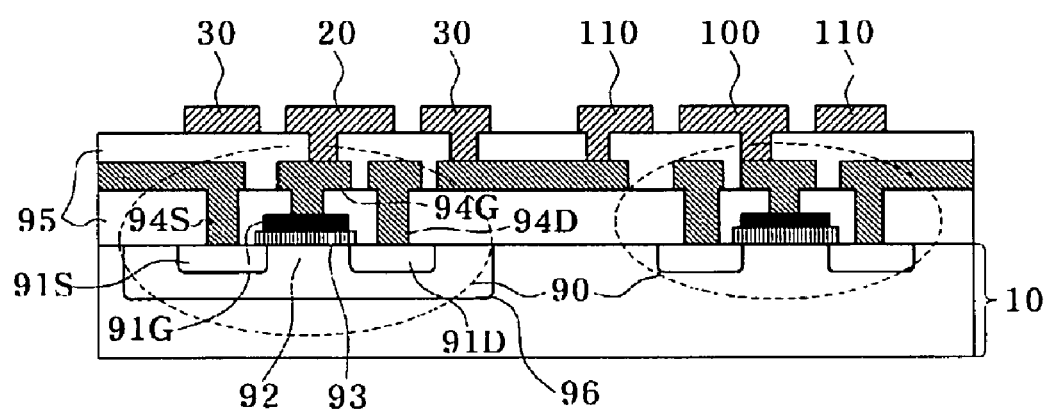

[Fig. 8]
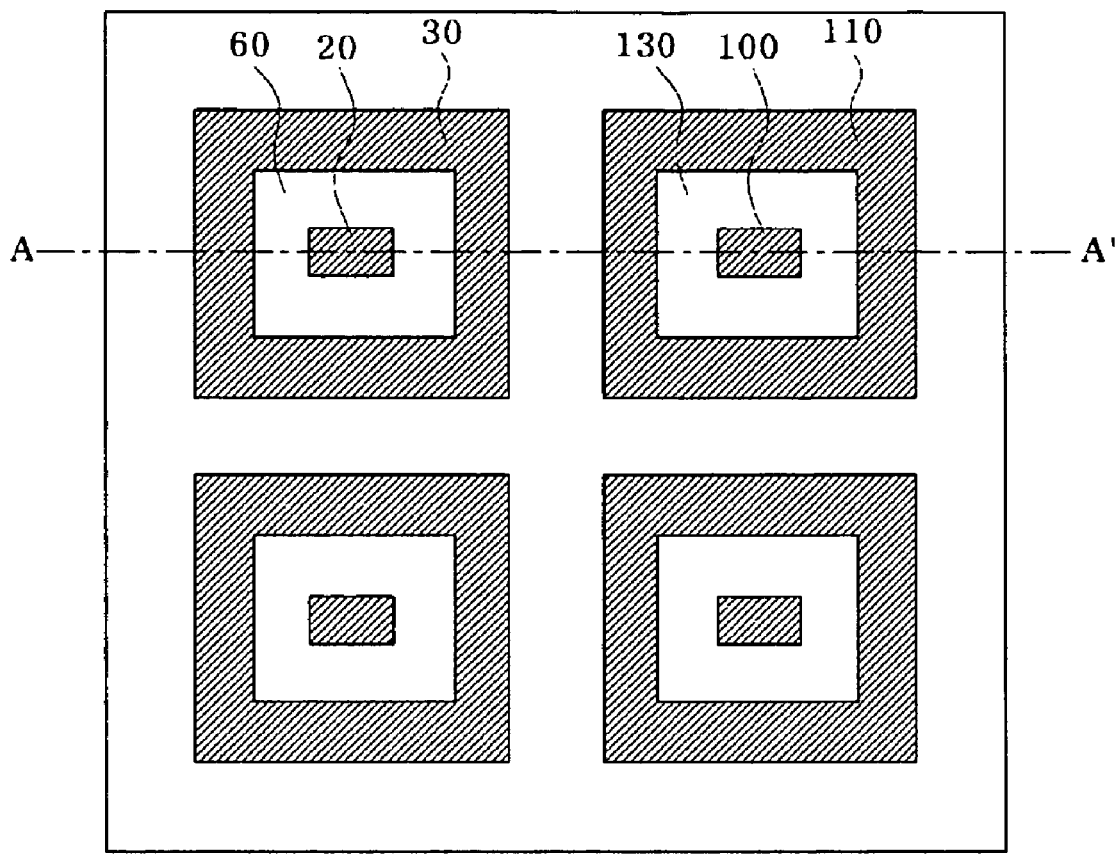
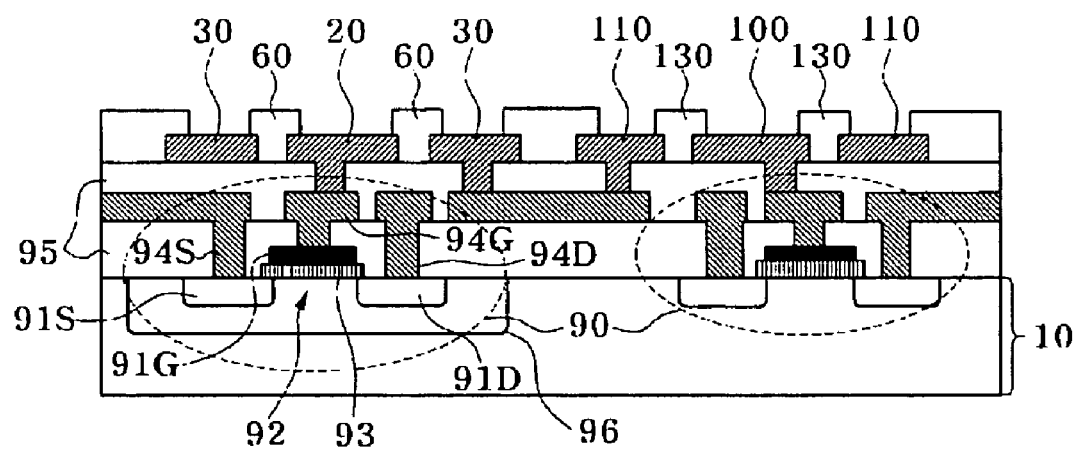

[Fig. 9]
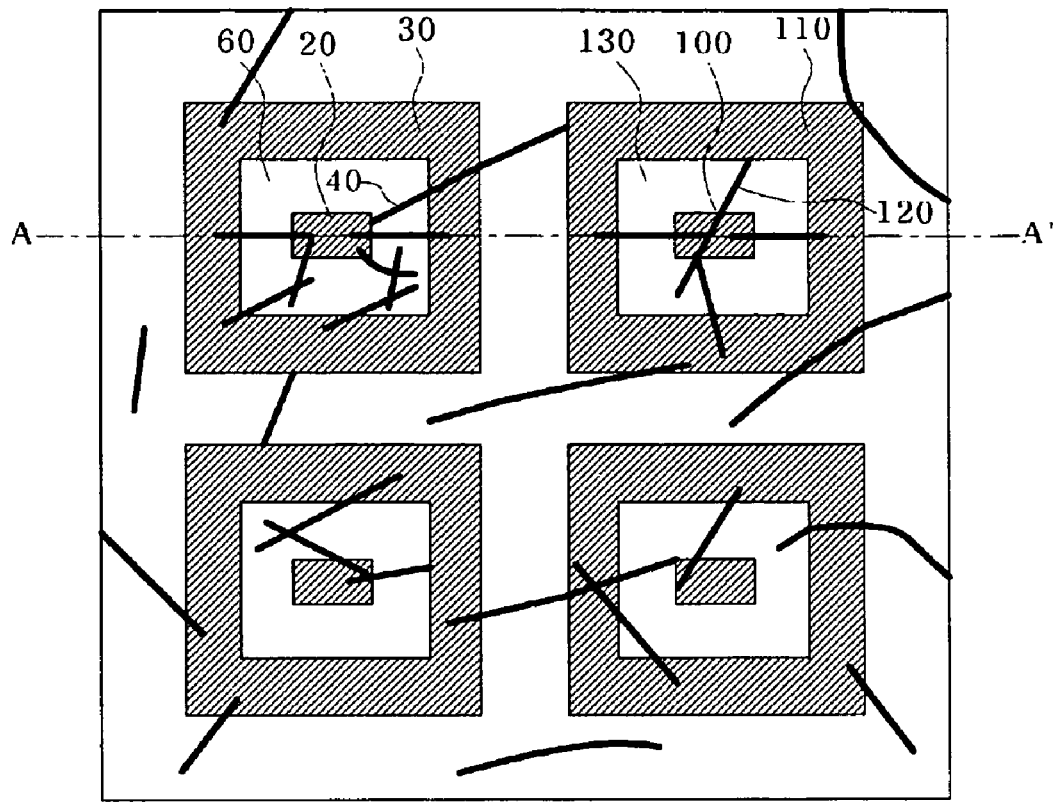
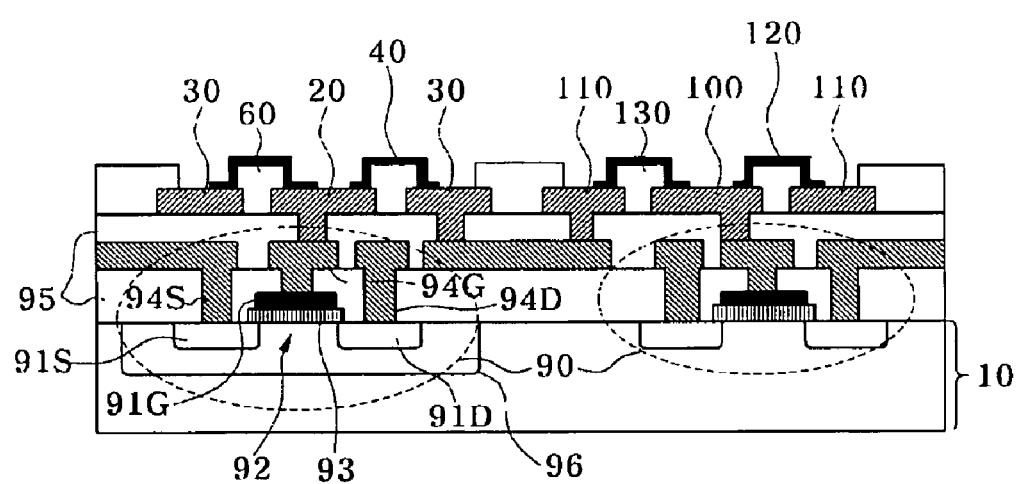

[Fig. 10]
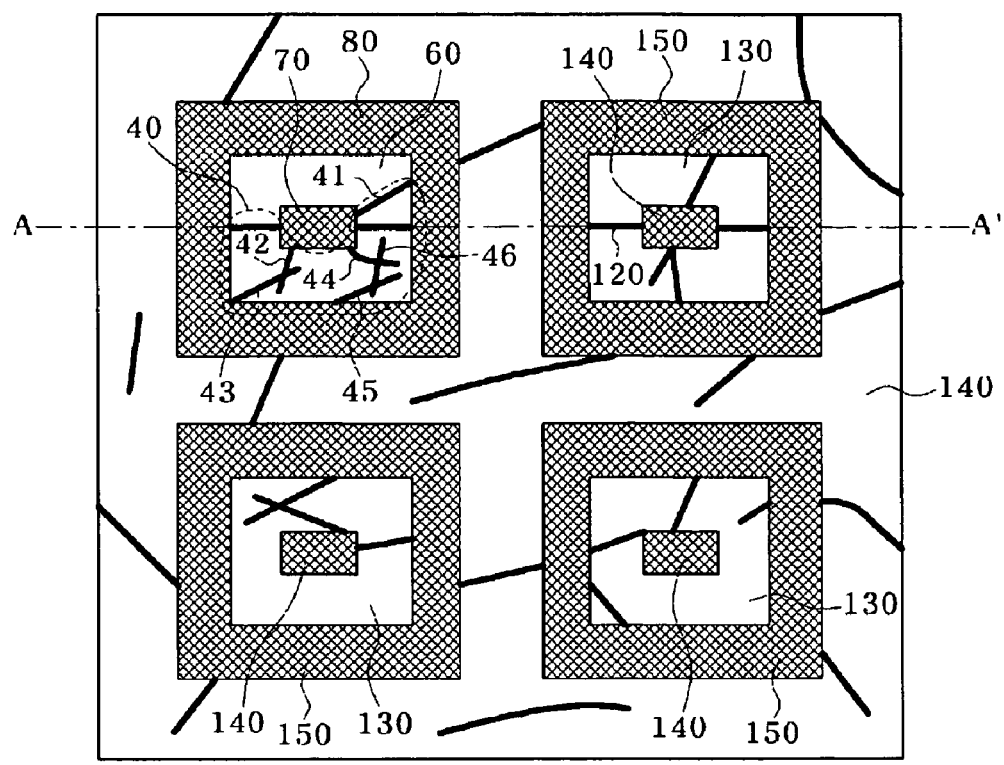
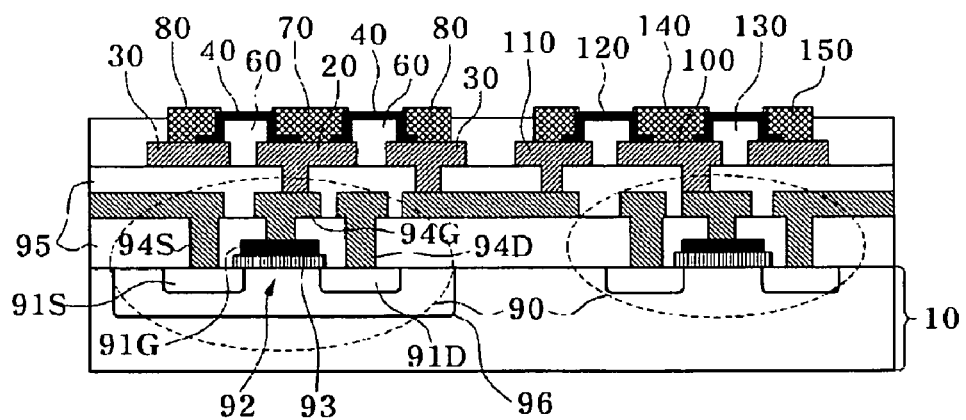

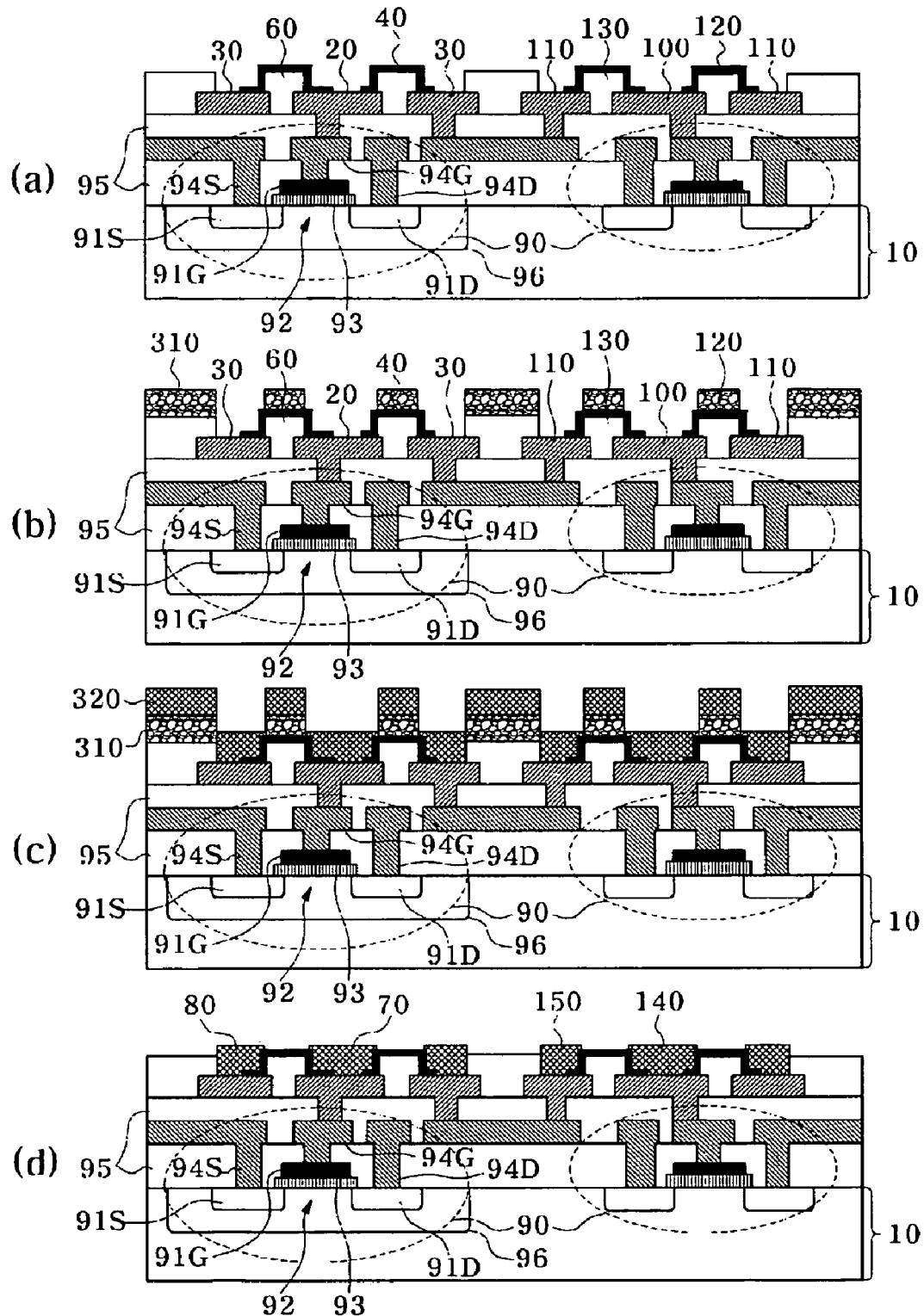
[Fig. 11]

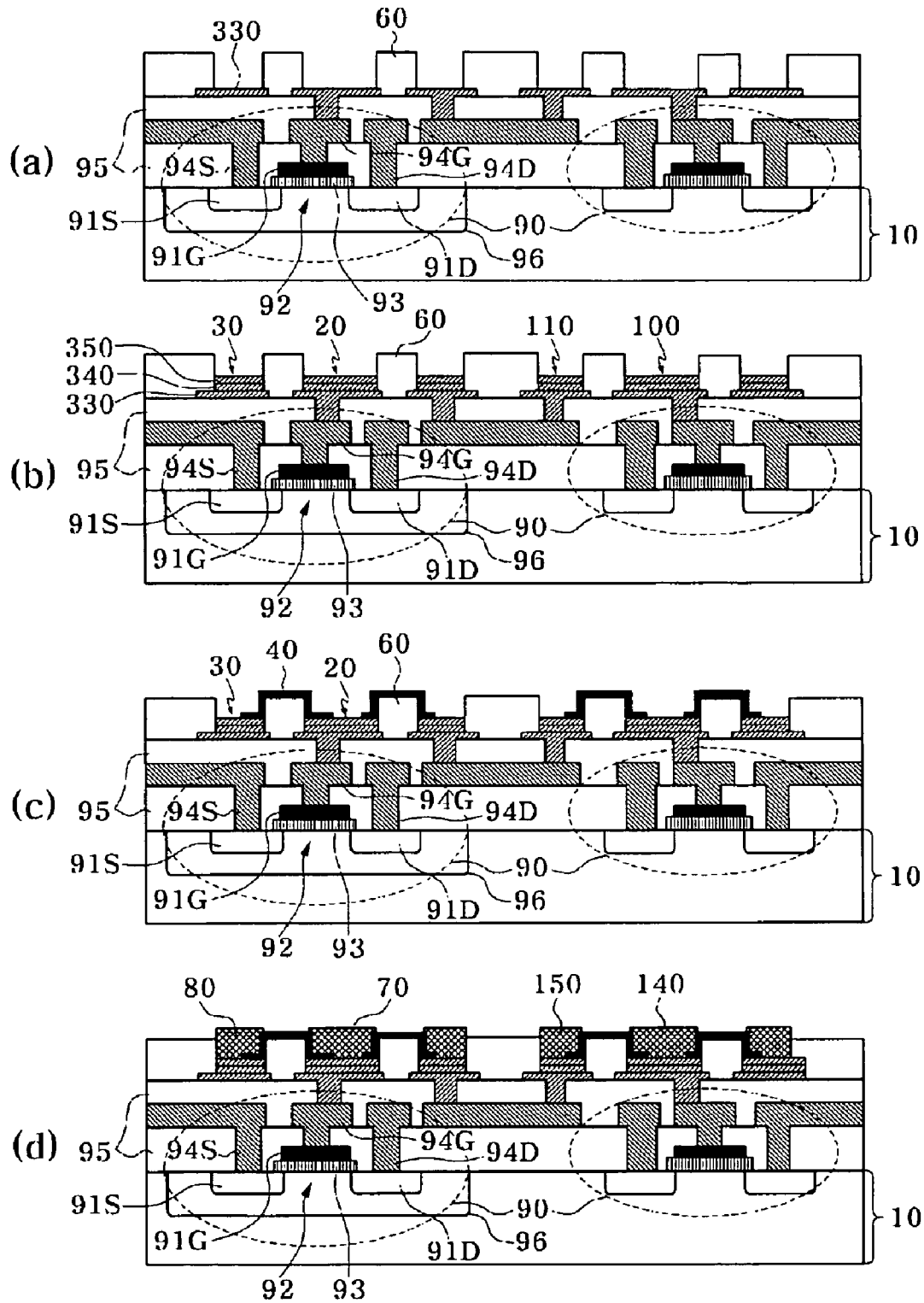
[Fig. 12]

NANOSTRUCTURE SENSORS

TECHNICAL FIELD

The present disclosure relates to sensors, such as sensors involving nanostructures.

BACKGROUND ART

Recently, interest in carbon nanostructures, such as carbon nanotubes, has increased in order to develop new chemical and biological sensors that utilize the sensitivity of the carbon nanotube to its surrounding environment. Some sensor strictures can be based on the various types of carbon nanotubes.

In one example, a conventional sensor based on the carbon nanotube can have multiple carbon nanotubes and square-shaped electrodes disposed at end portions of the carbon nanotubes. In accordance with the conventional sensor, when a reference voltage is applied to a second electrode, the carbon nanotube resistance can vary according to an object to be sensed, and a voltage or a current of a first electrode can vary according to the variation of the resistance of the carbon nanotube.

DISCLOSURE OF INVENTION

Technical Solution

The present disclosure describes techniques and structures for sensors that include nanostructures, in particular carbon nanostructures, such as carbon nanotubes.

In one aspect of the invention, embodiments feature a sensor that includes a substrate, a first electrode disposed on the substrate, and a second electrode disposed on the substrate. The second electrode is spaced apart from the first electrode and substantially surrounds the first electrode. At least one nanostructure contacts the first electrode and the second electrode, and the nanostructure is configured to vary an electrical characteristic according to an object to be sensed.

Advantageous implementations can optionally include one or more of the following features. The sensor can have an insulator disposed on the substrate between the first electrode and the second electrode. The sensor can also have a first conductor disposed on the first electrode, where a first portion of at least one nanostructure can be disposed between the first electrode and the first conductor. The sensor can also have a second conductor disposed on the second electrode, where a second portion of at least one nanostructure can be disposed between the second electrode and the second conductor.

In some embodiments, the second electrode may be a continuous electrode that completely surrounds the first electrode. In some embodiments, one or more electrodes may be non-continuous electrodes. In some embodiments, the second electrode may include gaps. In some embodiments, nanostructures do not extend through the gaps to contact any other electrode without contacting the desired surrounding electrode.

The sensor may include a MOSFET (Metal Oxide Semiconductor Field Effect Transistor) disposed under the first electrode and the second electrode, where at least one of a source, a gate and a drain of the MOSFET can be electrically connected to at least one of the first electrode and the second electrode. A reference voltage of a predetermined voltage can be applied to the second electrode. The first electrode can be divided into a first sub-electrodes spaced apart from one another. The nanostructure can include a carbon nanotube and can have a random arrangement.

The sensor may also include a first additional electrode disposed on the substrate, where the first additional electrode can be spaced apart from the first electrode and the second electrode. There can be a second additional electrode disposed on the substrate, where the second additional electrode can be spaced apart from the first electrode, the second electrode, the first additional electrode and the surrounding of the first additional electrode. There can be at least one additional nanostructure connected to the first additional electrode and the second additional electrode.

The sensor can be configured to sense in any of a liquid state, a gaseous state, or a carrier for the object to be sense. The nanostructure can include any of a nanotube, a nanowire, a nanorod, a nanoribbon, a nanofilm, or a nanoball.

In accordance with this second aspect of the invention, a sensor includes a substrate, and a second electrode disposed on the substrate. The second electrode has multiple holes. The sensor has a first electrode disposed in each of the holes, in which the first electrodes are spaced apart from the second electrode, and at least one nanostructure contacts the first electrode and the second electrode. The nanostructure is configured to vary an electrical characteristic according to an object to be sensed.

Advantageous implementations can optionally include one or more of the following features. The sensor can include an insulator providing an insulation between the first electrode and the second electrode. The sensor can have a first conductor disposed on the first electrode, where a first portion of at least one nanostructure can be disposed between the first electrode and the first conductor. The sensor can also have a second conductor disposed on the second electrode, where a second portion of the at least one nanostructure can be disposed between the second electrode and the second conductor.

The sensor can include a MOSFET (Metal Oxide Semiconductor Field Effect Transistor) disposed under the first electrode and the second electrode, where at least one of a sauce, a gate or a drain of the MOSFET can be electrically connected to at least one of the first electrode and the second, electrode. A reference voltage of a predetermined voltage can be applied to the second electrode. The nanostructures can include a carbon nanotube and can be randomly arranged in the sensor.

In accordance with this third aspect of the invention, a method for manufacturing a sensor includes preparing a substrate, and forming a first electrode and a second electrode on the substrate. The second electrode is spaced apart from the first electrode and surrounds the first electrode. The method includes forming at least one nanostructure to contact the upper surfaces of the first electrode and the second electrode.

Advantageous implementations can optionally include one or more of the following features. At least one nanostructure can be formed without a patterning process. The method can include forming an insulator disposed on the substrate between the first electrode and the second electrode carried out between the steps above. The method can include forming a first conductor disposed on the first electrode and a second conductor disposed on the second electrode, where a first portion of the at least one nanostructure can be disposed between the first electrode and the first conductor and a second portion of at least one nanostructure can be disposed between the second electrode and the second conductor.

The first conductor and the second conductor can be formed by a lift-off process. Each of the first conductor and the second conductor can be formed by a chemical plating process.

The method can also include forming an Al layer having shapes of the first electrode and the second electrode on the substrate, and exposing the substrate to a solution containing a Pd to form a Pd layer on the Al layer. The chemical plating can be carried cut by exposing the substrate to a solution containing an Au to form an Au layer on the Pd layer. The method can optionally involve exposing the substrate to a solution containing an Au to form an Au layer on the Pd layer. The chemical plating can be carried cut by exposing the substrate to the solution containing the Au to form an additional Au layer on the Au layer. The method can also involve carrying cut an annealing process.

The method can include forming an Al layer having shapes of the first electrode and the second electrode on the substrate, exposing at least the substrate to a solution containing a Pd to form a Pd layer on the Al layer, and exposing at least the substrate to a solution containing an Au to form an Au layer on the RI layer. The method can also involve forming a MOSFET (Metal Oxide Semiconductor Field Effect Transistor) disposed under the first electrode and the second electrode carried cut between the steps above.

At least one nanostructure can include a carbon nanotube, and at least one nanostructure can have a random arrangement. The method can include dipping the substrate in a solution having a carbon nanotube dispersed therein, and retrieving the substrate from the solution. The first electrode can be divided into first sub-electrodes by the second electrode.

A potential advantage of the method of manufacturing a sensor including a nanostructure as disclosed herein is that a patterning process for preventing a carbon nanotube from connecting a first electrode and an adjacent first electrode may not be required.

In general, in another potential advantage, embodiments feature a sensor including a nanostructure and a method for manufacturing the same that remains operational even when there is a carbon nanotube connecting a first electrode and an adjacent first electrode can remain connected to the carbon nanotube.

In general, in another potential advantage, embodiments feature a sensor including a nanostructure and a method for manufacturing the same, in which an electric potential of a liquid adjacent to a carbon nanotube can be maintained at a constant level.

Details of one or more implementations are set forth in the accompanying drawings and the description herein. Other features, aspects, and advantages will be apparent from the description, the drawings, and the claims.

Advantageous Effects

The method for manufacturing the sensor in accordance with the present invention can be advantageous in that the separate patterning process for patterning the nanostructure 40 is not required, thereby reducing a manufacturing cost of the sensor. Also, the method for manufacturing disclosed embodiments of the sensor can be advantageous in that the nanostructure 40 having the random arrangement can be deposited on the substrate 10 thereby allowing a low cost nanostructure formation process, such as dipping the substrate in the solution containing the nanostructures.

In conventional sensors that have nanostructures, accurate measurement may not be possible the to the interference through the nanostructure between the first electrode and an adjacent first electrode when the nanostructure is connected between the first electrode and the adjacent first electrode as the result of process error. In some embodiments of the current disclosure, this interference does not occur because the nanostructure is connected to the second electrode (where the reference voltage is applied to the second electrode) disposed between the first electrode and the adjacent first electrode, even when the nanostructure is connected between the first electrode and the adjacent first electrode. As a benefit, the sensor in accordance with the present invention can be robust to the process errors.

In conventional sensors, there can be interference obtaining accurate measurements became the electric potential of the object to be sensed that is adjacent to the nanostructure can be changed. In disclosed embodiments of the sensor, the second electrode having the reference voltage applied thereto can maintain the electric potential of the object to be sensed at a certain level. As a benefit, an accuracy of the measurement can be improved. More specifically, in conventional sensors, the second electrode having the reference voltage applied thereto may be disposed at one side of the object to be sensed that is adjacent to the nanostructure. With disclosed embodiments of the sensor, the second electrode having the reference voltage applied thereto can surround the object to be sensed adjacent to the nanostructure. As a benefit, the electric potential of the object to be sensed adjacent to the nanostructure can be maintained at the certain level to improve the accuracy of the measurement.

In other disclosed embodiments of the sensor, became an area of the second electrode is larger than that of the first embodiment, an effect of maintaining the electric potential of the object to be sensed can be greatly improved. As another benefit, a wiring connecting the second electrodes may be omitted.

Moreover, the disclosed embodiments of sensor with the nanostructure and their methods for manufacturing provide advantageous in that the resistances between the first electrode 20, and the second electrode 30 and the nanostructure can be improved when the first conductor 70 and the second conductor 80 are included (or the annealing process is carried cut). As a benefit, there can be increased accuracy of measurement.

Other disclosed embodiments of the sensor and their methods for manufacturing can be advantageous in that the separate patterning process of the first conductor 70 and the second conductor 80 may not be required when the first conductor 70 and the second conductor 80 are formed via the electroless plating process. As a benefit, there can be a reduction of manufacturing cost.

Also, disclosed embodiments of the sensor with the nanostructure and their methods for manufacturing can be advantageous in that the variation of the electrical characteristic of the nanostructure 40 may be amplified and/or converted to the digital signal directly at the substrate 10 when the sensor includes the MOSFET that may be used as the amplifier and/or the ADC. As a benefit, there can be improved accuracy of the measurement.

Other modifications are within the scope of the following claims.

BRIEF DESCRIPTION OF THE DRAWINGS

FIGS. 1A-1B illustrates plane and cross-sectional views of an example implementation of a sensor.

FIGS. 2A-2C illustrate example diagrams of a first electrode and a second electrode in the sensor.

FIGS. 3A-3B illustrate plane and cross-sectional views of an example of a sensor.

FIGS. 5A-10B illustrate examples of a method for manufacturing the sensor.

FIGS. 11A-12D illustrate examples of a method for manufacturing a first electrode, a second electrode, a first conductor, and a second conductor.

Like reference numbers and designations in the various drawings may indicate like elements.

MODE FOR THE INVENTION

Figure 4A:
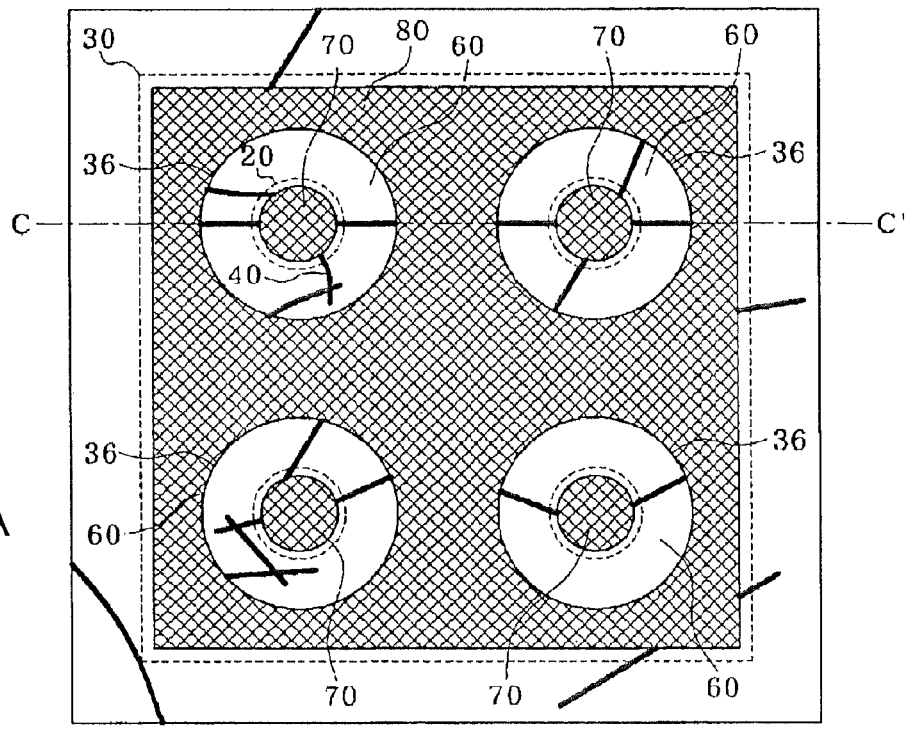
FIGS. 4A-4B illustrate plane and cross-sectional views of an example sensor.

Conventional sensors may not have the potential advantages of the various implementations of the current disclosure.

First, in order for the carbon nanotube to be connected only between the first electrode and the second electrode, that is, in order to prevent the carbon nanotube from being connected to an adjacent electrode as well as the first electrode and the second electrode, the carbon nanotube is required to be patterned, which can require an additional process (a photolithography process, for instance). The additional process increases a manufacturing cost of the conventional sensor. Therefore, the manufacturing cost of the sensor may be reduced when a technique that does not require the patterning of the carbon nanotube is developed.

Second, when the carbon nanotube connecting the first electrode and the adjacent electrode exists die to a process error despite the patterning process, a measurement accuracy of the sensor may be degraded, and the functionality of an IC chip including the sensor may be abolished in some severe cases. Therefore, the sensor yield may be improved when a technique that allows the sensor to operate normally is developed despite the carbon nanotube connecting the first electrode and the adjacent first electrode.

Third, when the object to be sensed is a liquid (or the object to be sensed is contained in a liquid), the resistance of the carbon nanotube may vary according to an electric potential of the liquid adjacent to the carbon nanotube. Since the electric potential of the liquid is variable, the measurement accuracy of the sensor may be degraded. Therefore, the measurement accuracy of the sensor may be improved when a technique that maintains the electric potential of the liquid adjacent to the carbon nanotube at a constant level is developed.

FIGS. 1A-1B illustrate respective plane and cross-sectional views of an example sensor. The plane view and the cross-sectional view taken along line A-A of the plane view are shown in FIGS. 1A-B, respectively.

Referring to FIG. 1B, the sensor includes a substrate 10, a first electrode 20, a second electrode 30 and at least one nanostructure 40. The sensor can also interact with a carrier for the object to be sensed 50, an insulator 60, a first conductor 70, a second conductor 80, and a metal oxide semiconductor field effect transistor 90 (referred to as "MOSFET" hereinafter). In some implementations, the carrier can be liquid, such as water, or a gas. In other implementations, the carrier can be in a liquid or gaseous state. In some implementations, the carrier can be a solution or in a solution. In some implementations, the object to be sensed can be electromagnetic radiation, such as IR radiation.

The sensor can also include at least one first additional electrode 100, at least one second additional electrode 110, additional nanostructures 120, additional insulators 130, at least one additional first conductor 140, and at least one additional second conductor 150.

Various types of substrates can be used as the substrate 10. For instance, the substrate 10 can be a semiconductor substrate (a silicon substrate, for instance), a silicon on insulator (SOI) substrate, a glass substrate, or a plastic substrate.

The first electrode 20 is formed on the substrate 10. The first electrode 20 can have various structures. For example, the first electrode 20 can be a single-layer structure or a multi-layer structure. In one embodiment, the first electrode 20 can include a single aluminum (Al) layer. In another embodiment, the first electrode 20 can include an Al layer and a palladium (Pd) layer disposed on the AI layer. In another embodiment, the first electrode 20 can include an Al layer, a Pd layer disposed on the Al layer and a gold (Au) layer disposed on the Pd layer.

While the first electrode 20 (or the first conductor 70) having a square shape is shown, the first electrode 20 can have other various shapes.

The second electrode 30 is also formed on the substrate 10. The second electrode 30 can have various structures similar to the first electrode 20. The second electrode 30 is formed to be spaced apart from the first electrode 20. Therefore, the second electrode 30 is not in direct contact with the first electrode 20. The second electrode 30 surrounds a side 21 of the first electrode 20.

In the embodiments described above, the second electrode completely encloses the first electrode on all sides. However, in other embodiments, there can be one or more gaps in the second electrode. In such embodiments, the second electrode can have a non-continuous structure. In some embodiments, the first and/or second electrodes may be non-continuous.

When gaps exist in the second electrode, the gaps can generally be small enough to reduce, e.g., make negligible, a likelihood of crosstalk between other strictures or other defects that degrade measurement accuracy of the sensor. For example, there can be crosstalk or other defects that degrade measurement accuracy of the sensor if a nanostructure extend through the gap to connect the wrong electrodes. In some embodiments, nanostructures do not extend through gaps to contact any other electrode without contacting the surrounding electrode. If the size of the gaps in the electrodes are kept small, there the likelihood that a yield of the sensors will be impacted can be reduced, e.g., the impact on chip yield made small, for example, less than the impact on yield from other process effects, or negligible. The yield and crosstalk may be impacted, more or less, by morphology of the nanostructure, which can depend on the composition and the processing conditions. The appropriate processing conditions generally can be determined experimentally.

Thus, "substantially surrounding" can refer to the second electrode continuously and completely enclosing the first electrode, or can refer to the second electrode surrounding the first electrode and having gaps that are sufficiently small to avoid significantly impacting yield.

In some embodiments, the electrodes may be located at an edge of the chip. In such embodiments, "substantially surrounding" can refer to the remaining available sides.

Although the second electrode 30 surrounds the side 21 of the first electrode 20, the second electrode 30 may not be on a same plane as the first electrode 20 in some embodiments. For example, in some embodiments the second electrode 30 may be elevated from the first electrode 20.

In some embodiments, a "side" of an electrode is a part of the electrode that surrounds a perimeter. In some embodiments, an inner perimeter of the second electrode can be spaced at a uniform distance, from an outer perimeter of the first electrode. In sixth embodiments, the side of the second electrode can be the inner perimeter and the side of the first electrode can be the alter perimeter of the first electrode.

In some embodiments, a reference voltage of a predetermined voltage can be applied to the second electrode 30. In these embodiments, a voltage or a current of the first electrode 20 can vary according to a variation of an electrical characteristic of the carbon nanotube 40. The reference voltage can be a power supply voltage or a ground voltage. While the second electrode 30 (or the second conductor 80) having a square ring shape is shown, the second electrode 30 can have other various shapes.

At least one nanostructure 40 is in contact with the first electrode 20 and the second electrode 30. In some embodiments, a first portion of the nanostructure 41 can be in contact with the first electrode 20, and a second portion of a first structure 41 can be in contact with the second electrode 30 in order for the first stricture 41 to establish the contact with the first electrode 20 and the second electrode 30. In another embodiment, a portion of a second nanostructure 42 can be in contact with the first electrode 20, a portion of a third nanostructure 43 can be in contact with the second electrode 30, and the second nanostructure 42 and the third nanostructure 43 can be in contact with each other in order for the nanostructures 42 and 43 to establish the contact with the first electrode 20 and the second electrode 30. In other embodiments, a portion of a fourth nanostructure 44 may be in contact with the first electrode 20, a portion of a fifth nanostructure 45 may be in contact with the second electrode 30, and the fourth nanostructure 44 and the fifth nanostructure 45 can be in contact with each other through a sixth nanostructure 46 in order for the nanostructures 44, 45 and 46 to establish the contact with the first electrode 20 and the second electrode 30. In some embodiments, the nanostructures can be dense, such as in a tangled mesh.

Various types of nanostructures, particularly carbon nanostructures, can be used as the nanostructure 40. For instance, a nanotube, nanowire, a nanorod, a nanoribbon, a nanoball, or a nanofilm can be used as the nanostructure 40. A carbon nanotube (CNT), a semiconductor nanowire, or a conductive polymer may be used as the nanostructure 40. The CNT can be classified into CNTs having characteristics of a metal and a semiconductor according to an electrical characteristic thereof and into a single-walled CNT, a double-walled CNT, and a multi-walled CNT according to a number of walls. At least one of various materials including tin oxide ($SnO_2$), zinc oxide (ZnO), indium oxide ($In_2O_3$), and cadmium oxide (CdO) can be used to constitute the semiconductor nanowire.

In some embodiments, some nanostructures can have a length much greater than their cross-sectional dimension. Such nanostructures can include wires, ribbons, and tubes. In some embodiments, these nanostructures may be disposed to lie on the underlying structure so that they extend generally parallel to the supporting surface.

An electrical characteristic of the nanostructure 40 changes according to the object to be sensed 50. The electrical characteristic can be a resistance. That is, the resistance of the nanostructure 40 can change according to whether the object to be sensed 50 exists or according to the amount or concentration of the object to be sensed 50. For instance, the object to be sensed 50 can be a protein, a deoxyribonucleic acid (DNA), a molecule or an ion. A functionalization for the nanostructure 40 to react to a specific object to be sensed can be carried cut such that the nanostructure 40 is selective, i.e., the electrical characteristic of the nanostructure 40 changes according to the specific object to be sensed among various objects to be sensed. In some implementations, the functionalization can involve nanostructures in sensors that can detect one or more electrical characteristics to detect proteins, tumor markers, molecules, and certain viruses in solutions. The nanostructure 40 used for the sensor in accordance with the present invention may have a random arrangement.

In some embodiments, the object to be sensed 50 can be in a liquid state or a gaseous state. Alternatively, the object to be sensed 50 can be contained in a liquid or a gas. In some embodiments, the object can be a molecule, such as a complex molecule. The molecule may be in a solution.

The insulator 60 is formed on the substrate 10 between the first electrode 20 and the second electrode 30. The nanostructure 40 is disposed on an upper surface of the insulator 60.

The first conductor 70 is disposed on the first electrode 20 having the at least one nanostructure 40 therebetween such that a first portion of the at least one nanostructure 40 is disposed between the first electrode 20 and the first conductor 70. The first conductor 70 can be an Au layer.

The second conductor 80 is disposed on the second electrode 30 having the at least one nanostructure 40 therebetween. A second portion of the at least one nanostructure 40 is disposed between the second electrode 30 and the second conductor 80. The second conductor 80 may be the Au layer.

The MOSFET 90 is disposed under the first electrode 20 and the second electrode 30. While a gate 91G of the MOSFET 90 electrically connected to the first electrode 20 is shown, it is sufficient when at least one of the gate 91G, a source 91S, and a drain 91D of the MOSFET 90 is electrically connected to one of the first electrode 20 and the second electrode 30. The MOSFET 90 includes the gate 91G, the source 91S, the drain 91D, a channel region 92, a gate oxide film 93, a gate electrode 94G, a source electrode 94S, a drain electrode 94D, and an insulation film 95. The MOSFET 90 can also include a well 96. The MOSFET 90 in the lower left side of the cross-sectional view of FIG. 1B is a PMOS device (P-channel Metal-Oxide Semiconductor Field Effect Transistor), in which a source region and a gate region are doped with a p-type impurity, and a well is doped with an n-type impurity. The MOSFET 90 on the lower right side of the cross-sectional view of FIG. 1B is an NMOS device (N-channel Metal-Oxide Semiconductor Field Effect Transistor), in which a source region and a gate region are doped with the n-type impurity, and a substrate is a p-type substrate. The MOSFET 90 may be used as a part of a CMOS (Complementary Metal Oxide Semiconductor) circuit formed on the substrate 10. The CMOS circuit can be used as an amplifier, an analog-to-digital converter (ADC), or a switch for selecting one of the electrodes 20 and 100. In some embodiments, a digital signal corresponding to the variation of the electrical characteristic of the nanostructure 40 can be generated.

The sensor can have an array structure, including multiple first electrodes and second electrodes. More specifically, the sensor can include the first additional electrode 100, at least one second additional electrode 110, and additional nanostructures 120. Also, the sensor can include multiple additional insulators 130, at least one additional first conductor 140, and at least one additional second conductor 150.

The one first additional electrode 100 can be formed on the substrate 10 to be spaced apart from the first electrode 20 and the second electrode 30. Each of the first additional electrodes 100 can be surrounded by each of second additional electrodes 110 that correspond to the respective first additional electrodes 100.

The second additional electrode 110 can be formed on the substrate 10 to be spaced apart from the first electrode 20, the second electrode 30, and the first additional electrode 100.

Of the additional nanostructures 120, at least one nanostructure can be connected to one of the corresponding first additional electrodes of the additional electrode 100 and the corresponding second additional electrode of the second additional electrode 110.

FIGS. 2A-C are diagrams illustrating various examples of the first electrode 20 and the second electrode 30 (the first conductor 70 and the second conductor 80) that can be employed in the sensor.

Referring to FIG. 2A, the first electrode 20 (or the first conductor 70) has a circular shape, and the second electrode 30 (or the second conductor 80) has a ring shape.

Referring to FIG. 2B, the first electrode 20 (or the first conductor 70) includes multiple protruding portions 21 and multiple concaved portions 22. The second electrode 30 (or the second conductor 80) includes multiple protruding portions 31 and multiple concaved portions 32. The protruding portions 31 of the second electrode extend into the concaved portions 22 of the first electrode, and the protruding regions 21 of the first electrode extend into the concaved portions 32 of the second electrode. When the first electrode 20 and the second electrode 30 (or the first conductor 70 and the second conductor 80) have such shapes, the sides of the first electrode 20 and the second electrode 30 can be increased to improve a sensitivity. Referring to FIG. 2C, the first electrode 20 (or the first conductor 70) can be divided into multiple first sub-electrodes 23. The multiple first sub-electrodes 23 are spaced apart from one another. When the first electrode 20 has such a shape, the first sub-electrodes 23 having a superior characteristic can be selected and used from the multiple first sub-electrodes 23. For instance, because the nanostructure has a random arrangement, the nanostructure may not be connected between the second electrode 30 and one of the first sub-electrodes 23, a desired number of the nanostructures may be connected between the second electrode 30 and another of the first sub-electrodes 23, or an excessive number of the nanostructures may be connected between the second electrode 30 and yet another of the first sub-electrodes 23.

In some embodiments, a desired or appropriate number of nanostructures may be determined by a type of structure or an electrical characteristic. For instance, in case it is facile to measure the variation of the resistance when the resistance between the second electrode and the first sub-electrode is 10 KOhm-100 KOhm, the first sub-electrode having such resistance may be selected from multiple sub-electrodes. In another embodiment, when the first electrode is divided into multiple the sub-first electrodes, an average value of the electrical characteristics measured at the multiple sub-electrodes may be used. Sometimes this can be potentially advantageous since using the average value can be generally insensitive to an occurrence of an error compared to using an electrical characteristic measured at a single first electrode. Therefore, the first sub-electrode 23 having a desired number of the nanostructures connected thereto may be selected and used as the first sub-electrode with the superior characteristic.

FIGS. 3A-3B illustrate a respective a plane view and a cross-sectional view taken along line B-B of the plane view of an example sensor. In FIGS. 3A-B, a sensor is shown that does not include a MOSFET.

Referring to FIGS. 3A-B, the sensor can include a substrate 10, a first electrode 20, a second electrode 30, at least one nanostructure 40, and an object to be sensed 50. The sensor can include a first insulator 60, a first pad 210, a second pad 220, a first wiring 230, a second wiring 240, and a second insulator 250. Although not shown, the sensor can have a second conductor disposed on a first conductor and the second electrode 30.

The sensor has the MOSFET to amplify the variation of the electrical characteristic of the nanostructure 40 and/or to convert the variation to the digital signal. The variation of the electrical characteristic of the nanostructure 40 can be outputted via the first wiring 230 and the first pad 210 became the sensor, in some embodiments, may not include the MOSFET.

Since the MOSFET is not required in some embodiments, a low-cost plastic substrate or glass substrate can be used for the sensor.

Figure 4B:
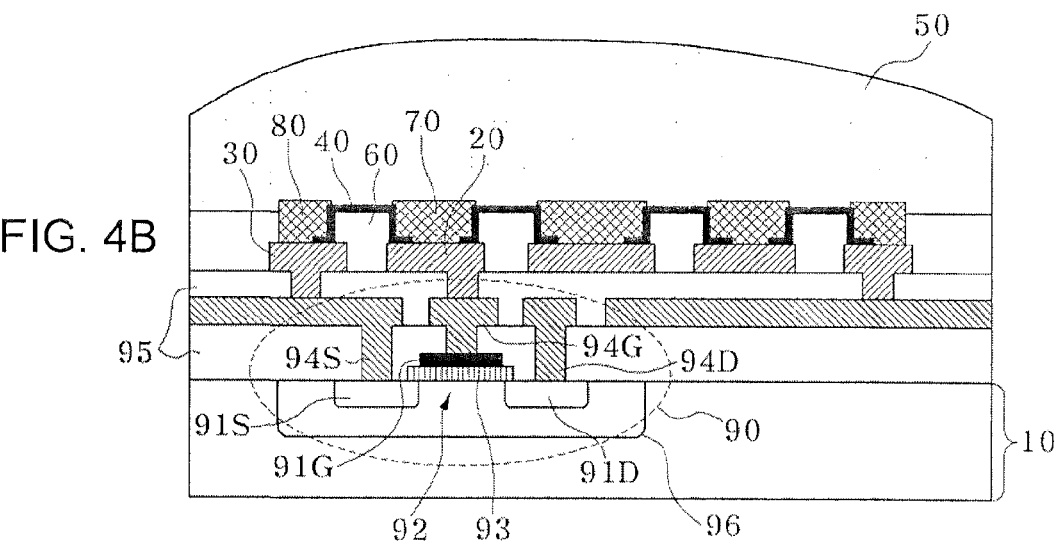

FIGS. 4A and 4B illustrate a respective a plane view and a cross-sectional view taken along line C-C of the plane view of an example sensor. Referring to FIGS. 4A-B, the sensor includes a substrate 10, first electrodes 20, a second electrode 30, nanostructures 40, and an object to be sensed 50. The sensor can include an insulator 60, first conductors 70, a second conductor 80, and a MOSFET 90.

The first electrodes can be formed on the substrate 10. Similar to the embodiments shown in FIGS. 1A-2C, the first electrodes 20 can have various structures and shapes.

The second electrode also can be formed on the substrate 10. A number of holes 36 can be formed in the second electrode 30. At least one of the first electrodes 20 corresponding to each of the holes is disposed in the holes and spaced apart from the second electrode 30. Similar to the embodiments of FIGS. 1A-2C, the second electrode 30 can have various structures and shapes. In some embodiments, a reference voltage of a predetermined voltage can be applied to the second electrode 30.

The insulators 60 can provide an insulation between the first electrodes 20 and the second electrode 30.

The first conductors 70 are disposed on the first electrodes 20 having the nanostructures 40 there between. The first conductor 70 can be an Au layer. First electrode 20 and second electrodes 30 are illustrated in FIG. 4A.

The structures of the substrate 10, the nanostructure 40, the object to be sensed 50, and the MOSFET 90 can be identical to those of other described embodiments.

In accordance with conventional sensors that include nanostructures, an accurate measurement may not possible the to an interference through the nanostructure between the first electrode and an adjacent first electrode when the nanostructure is connected between the first electrode and the adjacent first electrode as a result of a process error. This interference does not occur in the disclosed embodiments at least became the nanostructure is connected to the second electrode (where the reference voltage is applied to the second electrode) disposed between the first electrode and the adjacent first electrode, even when the nanostructure is connected between the first electrode and the adjacent first electrode. As a potential advantage, the sensor in accordance with embodiments of the present invention is robust to process errors.

In accordance with the conventional sensors, there can be interference getting an accurate measurement because an electric potential of the object to be sensed adjacent to the nanostructure can be changed. In the embodiments of the current disclosure, the second electrode having the reference voltage applied thereto can maintain the electric potential of the object to be sensed at a certain level. As a benefit, an accuracy of the measurement is improved. More specifically, in accordance with the conventional sensors, the second electrode having the reference voltage applied thereto is disposed at one side of the object to be sensed adjacent to the nanostructure. In embodiments of the current disclosure, the second electrode having the reference voltage applied thereto can surround the object to be sensed adjacent to the nanostructure. As a result, the electric potential of the object to be sensed adjacent to the nanostructure can be maintained at the certain level to thereby improve the accuracy of the measurement.

FIGS. 5A through 10B are diagrams that illustrate steps of an example method for manufacturing the sensor. Plane views and cross-sectional views taken along line A-A of the plane views are shown in an upper portion and lower a portion of FIGS. 5A through 10B, respectively. Since the methods for manufacturing the sensor in accordance with the second embodiment and the third embodiment of the present invention may be deduced from the method for manufacturing, the sensor will be described with respect to the embodiments of FIGS. 1A-4B.

FIGS. 5A-B illustrate the preparation of the substrate 10. Various types of substrates can be used, such as the semiconductor substrate.

FIGS. 6A-B illustrate the formation of the MOSFET 90. A reference numeral 97 denotes a wiring for connecting the second electrode 30 and the first additional electrode 100.

FIGS. 7A-B show that the first electrode 20 and the second electrode 30 are formed on the substrate 10 so that the second electrode 30 is spaced apart from the first electrode 20 and surrounds a side of the first electrode 20. The first additional electrode 100 and the second additional electrode 110 are also formed.

FIGS. 8A-B show that the insulator 60 is formed on the substrate 10. The insulator 60 is disposed between the first electrode 20 and the second electrode 30. At the same time, the additional insulator 130 is also formed. The insulator 60 can include silicon dioxide (SiO2). While an example where the insulator 60 is formed after the first electrode 20 and the second electrode 30 are formed is shown, a portion of the first electrode and the second electrode can be formed first, the insulator 60 is formed next, and then the rest of the first electrode 20 and the second electrode 30 may be formed. In some embodiments, when the first electrode 20 and the second electrode 30 include a sequentially stacked layer of the aluminum (Al) layer, the palladium (Pd) layer and the gold (Au) layer, the aluminum (Al) layer, the insulator 60, the palladium (Pd) layer and the gold (Au) layer can be sequentially formed. In other embodiments, when the first electrode 20 and the second electrode 30 have a sequentially stacked layer of the aluminum (Al) layer and the palladium (Pd) layer, the aluminum (Al) layer, the insulator 60 and the palladium (Pd) layer can be sequentially formed.

FIGS. 9A-B, at least one nanostructure 40 contacting upper surfaces of the first electrode 20 and the second electrode 30 is formed. At approximately the same time, the additional nanostructure 120 is also formed. The nanostructure has a random arrangement. In some embodiments, the nanostructure can be formed by dipping the substrate 10 in a solution having the nanostructure (the carbon nanotube, for instance) dispersed therein and retrieving the substrate 10 from the solution. The solution having the carbon nanotubes dispersed therein can be obtained by mixing the carbon nanotubes with a 1,2-dichlorobenzene at a ratio of 0.02 g:200 ml. The dipping of the substrate can be carried out for 1 to 5 minutes, and a speed of the retrieving of the substrate can range from 1 to 10 mm/min.

FIGS. 10A-B further illustrate the example method for manufacturing the sensor. FIG. 10B shows that the first conductor 70 and the second conductor 80 are formed on the first electrode 20 and the second electrode 30, respectively. At the same time, the additional first conductor 140 and the additional second conductor 150 are formed. The first conductor 70 can be used to improve a resistance between the first electrode 20 and the nanostructure 40, and the second conductor 80 can be used to improve a resistance between the second electrode 30 and the nanostructure 40. The first conductor 70 and the second conductor 80 can be formed via various methods. For instance, the first conductor 70 and the second conductor 80 can be formed via a patterning process or a non-patterning process, i.e. a self-align process. The patterning process can include a lift-off process. The non-patterning process can include a chemical plating process. More specifically, the chemical plating process can include an electroplating process, such as an electroless plating process.

In other embodiments, instead of the process for forming the first conductor 70 and the second conductor 80, the resistances between the first conductor 70, the second conductor 80 and the nanostructure 40 can be improved via an annealing process. The nanostructure 40 can then be exposed to the object to be sensed 50 as shown in FIG. 1B.

FIGS. 11A-D and 12A-D are diagrams illustrating various examples of the method for manufacturing the first electrode 20 and the second electrode 30 and the first conductor 70 and the second conductor 80.

FIGS. 11A-D illustrate an example where the first conductor 70 and the second conductor 80 are formed via the lift-off process. FIGS. 11A-D show that after the nanostructure 40 is formed on the substrate 10 (FIG. 11A), a photoresist film is formed on the substrate 10. The photoresist film is then exposed and developed to form a photoresist film pattern 310 covering an entirety of the structure except an upper portions of the first electrode 20, the second electrode 30, at least one first additional electrode 100, and at least one second additional electrode 110 (FIG. 11B). Thereafter, a conductor 320, such as an Au conductor, is deposited on the photoresist film pattern 310 (FIG. 11C). The conductor 320 on the photoresist film pattern 310 and the photoresist film pattern 310 are then removed such that the first conductor 70 and the second conductor 80 formed on the first electrode 20 and the second electrode 30 remain FIG. 11D.

FIGS. 12A-D illustrate an example wherein the first conductor 70 and the second conductor 80 are formed via the chemical plating process, such as the electroless plating process. Particularly, the example exemplifies the first electrode 20 and the second electrode 30 having the aluminum (Al) layer, the palladium (Pd) layer and the gold (Au) layer, where the aluminum (Al) layer, the insulator 60, the palladium (Pd) layer and the gold (Au) layer are sequentially formed.

FIG. 12, an Al layer (or any well-known conductive layer) 330 having a shape of the first electrode 20 and the second electrode 30 and the insulator 60 are formed on the substrate 10 FIG. 12A.

Thereafter, a Pd layer 340 is formed on a surface of the Al layer 330, and an Au layer 350 is formed on the Pd layer 340 (FIG. 12B). The process for forming the Pd layer 340 can be carried out by exposing an upper surface of the substrate 10 to a solution containing a Pd (also referred to as a Pd activated solution). The solution containing the Pd may contain a palladium chloride (PdCl2) 0.1 g, a hydrochloric acid (HCl) 3 ml, a phosphoric acid (H3PO4) (85%) 3 ml, a magnesium (Mg) solution 6 ml, a PEG (Polyethylene glycol) solution 1 ml, and a deionized water. The process for exposing the upper surface of the substrate 10 to the solution containing the Pd may be carried out by dipping the substrate 10 in the solution containing the Pd for 3 minutes at a room temperature and then cleaning the substrate 10. When the upper surface of the substrate 10 is exposed to the solution containing the Pd, the Pd layer 340 is formed only on the Al layer 330 and not on a surface of the insulator 60. As a potential benefit, the formation process of the Pd layer 340 does not require a separate patterning process. Since the Au is plated using the Pd layer 340 as a catalyst, the Pd layer 340 can help in the deposition of the Au. The process for forming the Au layer 350 via the electroless plating process can be carried out by exposing the upper surface of the substrate 10 to a solution containing the Au (also referred to as a gold plating solution). The solution containing the Au can include a solution of potassium cyanide (KCN) 0.06 g, citric acid 0.9 g, gold potassium cyanide (KAuCN2) 0.1 g, hydrazine (N2H4) 2 ml, and deionized water 50 ml. The process for exposing the upper surface of the substrate 10 to the solution containing the Au can be carried out by dipping the substrate 10 in the solution containing the Pd for 1 hour and 20 minutes at 50° C. and then cleaning the substrate 10. When the upper surface of the substrate 10 is exposed to the solution containing the Au, the Au layer 350 is formed only on the Pd layer 340 and not on a surface of the insulator 60. As a potential benefit, the process of forming the Au layer 350 does not require the separate patterning process. The nanostructure 40 is then formed on the Pd layer 340 and the insulator 60 (FIG. 12C).

Afterwards, an additional Au layer 360 corresponding to the first conductor 70 and the second conductor 80 is formed on the Au layer 350 (FIG. 12D). The process for forming the Au layer 360 via the electroless plating process can be carried out by exposing the upper surface of the substrate 10 to the solution containing the Au. The solution containing the Au can include KCN 0.06 g, citric acid 0.9 g, KAuCN2 0.1 g, hydrazine 2 ml, and deionized water 50 ml. The process for exposing the upper surface of the substrate 10 to the solution containing the Au can be carried out by dipping the substrate 10 in the solution containing the Pd for 15 minutes at 50° C. and then cleaning the substrate 10. When the upper surface of the substrate 10 is exposed to the solution containing the Au, the Au layer 360 is formed only on the Au layer 350 and not on a surface of the insulator 60. As a potential benefit, the formation process the Au layer 360 does not require the separate patterning process.

The chemical plating process shown in FIGS. 12A-D can be diversely varied. In some embodiments, instead of forming the additional conductive layer 360 corresponding to the first conductor 70 and the second conductor 80, the annealing process can be carried out. The resistances between the first electrode 20, the second electrode 30 and the nanostructure 40 can be reduced by the annealing process. In other embodiments, the process for forming the Au layer 350 included in the first electrode 20 and the second electrode 30 can be omitted. Other modifications are within the scope of the following claims.

The invention claimed is:

1. A sensor comprising:
a substrate;
a first electrode disposed on the substrate;
a second electrode disposed on the substrate, the second electrode being spaced apart from the first electrode and circumscribing at least all sides along at least one axis of the first electrode; and
at least one nanostructure contacting the first electrode and the second electrode, the at least one nanostructure configured to vary an electrical characteristic according to an object to be sensed;
wherein the object to be sensed comprises a solution, a liquid, a gas, a molecule, a protein, a virus, a marker, an acid, an ion, an impurity, an electromagnetic radiation, or a particle, and
wherein the electrical characteristic comprises a voltage, a current, a resistance or a conductance.

2. The sensor in accordance with claim 1, further comprising an insulator disposed on the substrate between the first electrode and the second electrode.

3. The sensor in accordance with claim 2, further comprising:
a first additional electrode disposed on the substrate, the first additional electrode being spaced apart from the first electrode and the second electrode;
a second additional electrode disposed on the substrate, the second additional electrode being spaced apart from the first electrode, the second electrode and the first additional electrode and surrounding the first additional electrode; and
at least one additional nanostructure connected to the first additional electrode and the second additional electrode.

4. The sensor in accordance with claim 1, further comprising:
a first conductor disposed on the first electrode, a first portion of the at least one nanostructure being disposed between the first electrode and the first conductor; and
a second conductor disposed on the second electrode, a second portion of the at least one nanostructure being disposed between the second electrode and the second conductor.

5. The sensor in accordance with claim 1, further comprising a metal oxide semiconductor field effect transistor (MOSFET) disposed under the first electrode and the second electrode, wherein at least one of a source, a gate and a drain of the MOSFET is configured for an electrical connection with at least one of the first electrode and the second electrode.

6. The sensor in accordance with claim 1, wherein the sensor is configured for application of a reference voltage of a predetermined voltage to be applied to the second electrode.

7. The sensor in accordance with claim 1, wherein the first electrode comprises a plurality of first sub-electrodes spaced apart from one another.

8. The sensor in accordance with claim 7, wherein the sensor is configured to average a value of electrical characteristics of at least two of the first sub-electrodes.

9. The sensor in accordance with claim 1, wherein the at least one nanostructure comprises a carbon nanotube.

10. The sensor in accordance with claim 1, wherein the at least one nanostructure has a random arrangement with at least one other nanostructure.

11. The sensor in accordance with claim 1, wherein the sensor is configured to sense the object to be sensed in any of a liquid state, a gaseous state, or a carrier for the object to be sensed.

12. The sensor in accordance with claim 1, wherein the nanostructure comprises any of a nanotube, a nanowire, a nanorod, a nanoribbon, a nanofilm, or a nanoball.

13. The sensor of claim 1, wherein the second electrode surrounds an entire outer perimeter of the first electrode in at least the one axis.

14. The sensor of claim 1, wherein the second electrode substantially surrounds both sides of the first electrode that are parallel to the axis of the first electrode.

15. The sensor of claim 1, wherein the second electrode substantially surrounds opposite sides of the first electrode.

16. A sensor comprising:
a substrate;
a first electrode disposed in each of a plurality of holes;
a second electrode disposed on the substrate, the second electrode having the plurality of holes, the first electrode being spaced apart from the second electrode, the second electrode being configured to circumscribe at least all sides along at least one axis of the first electrode; and at least one nanostructure contacting the first electrode and the second electrode, the at least one nanostructure configured to vary an electrical characteristic according to an object to be sensed, wherein the object to be sensed comprises a solution, a liquid, a gas, a molecule, a protein, a virus, a marker, an acid, an ion, an impurity, an electromagnetic radiation, or a particle, and wherein the electrical characteristic comprises a voltage, a current, a resistance or a conductance.

17. The sensor in accordance with claim 16, further comprising an insulator providing an insulation between the first electrode and the second electrode.

18. The sensor in accordance with claim 16, further comprising a first conductor disposed on the first electrode, a first portion of the at least one nanostructure being disposed between the first electrode and the first conductor; and a second conductor disposed on the second electrode, a second portion of the at least one nanostructure being disposed between the second electrode and the second conductor.

19. The sensor in accordance with claim 16, further comprising a (metal oxide semiconductor field effect transistor (MOSFET) disposed under the first electrode and the second electrode, wherein at least one of a source, a gate or a drain of the MOSFET is configured for an electrical connection with at least one of the first electrode and the second electrode.

20. The sensor in accordance with claim 16, wherein a reference voltage of a predetermined voltage is applied to the second electrode.

21. The sensor in accordance with claim 16, wherein the at least one nanostructures comprises a carbon nanotube.

22. The sensor in accordance with claim 16, wherein the at least one nanostructure is randomly arranged in the sensor.

23. The sensor of claim 16, wherein the second electrode surrounds an entire outer perimeter of the first electrode in at least the one axis.

24. The sensor of claim 12, wherein the second electrode substantially surrounds both sides of the first electrode that are parallel to the axis of the first electrode.

25. The sensor of claim 16, wherein the second electrode substantially surrounds opposite sides of the first electrode.

26. A method for operating a sensor comprising a first electrode, a second electrode, and a first nanostructure configured to be electrically coupled in series between the first and second electrodes, the method comprising:

accessing an object to be sensed, the object comprising a solution, a liquid, a gas, a molecule, a protein, a virus, a marker, an acid, an ion, an impurity, electromagnetic radiation, or a particle;

enabling the sensor for operation with at least the second electrode circumscribing at least all sides along at least one axis of the first electrode while the first and second electrodes are physically separated;

applying a reference voltage to the second electrode;

detecting an electrical characteristic associated with the first nanostructure when the first nanostructure is exposed to the object to be sensed, wherein the first nanostructure is configured to vary the electrical characteristic when the first nanostructure is exposed to the object, wherein the electrical characteristic comprises a voltage, a current, a resistance or a conductance; and reading the electrical characteristic from at least one of the first or second electrodes of the sensor.

27. The method in accordance with claim 26, further comprising applying and maintaining an electric potential of a liquid adjacent to the first nanostructure at a constant level.

28. The method in accordance with claim 26, further comprising detecting the electrical characteristic accurately when the first nanostructure is coupled to an additional first electrode.

29. The method in accordance with claim 26, wherein the sensor utilizes a MOSFET (metal oxide semiconductor field effect transistor) disposed under the first electrode and the second electrode, wherein at least one of a source, a gate and a drain of the MOSFET is configured for an electrical connection with at least one of the first electrode and the second electrode.

30. The method in accordance with claim 29, further comprising modulating the read electrical characteristic with the MOSFET to amplify the read electrical characteristic or convert the read electrical characteristic to a digital signal.

31. The method in accordance with claim 29, further comprising using the MOSFET as a switch between the first and second electrodes.

32. The method in accordance with claim 26, wherein the detecting comprises measuring a reaction of the first nanostructure when the first nanostructure is exposed to an object to be sensed.

33. The method in accordance with claim 26, wherein the first electrode comprises a plurality of first sub-electrodes that are separated from one another.

34. The method in accordance with claim 33, wherein the detecting comprises measuring a variation of a resistance between the second electrode and at least two of the first sub-electrodes.

35. The method in accordance with claim 33, wherein the detecting comprises averaging a value of electrical characteristics of at least two of the first sub-electrodes.

36. The method in accordance with claim 26, further comprising enabling the first nanostructure to operate with any of a carbon nanostructure, a nanotube, a nanowire, a nanorod, a nanoribbon, a nanoball, or a nanofilm.

37. The method in accordance with claim 26, further comprising enabling the sensor to operate with a plurality of nanostructures in a random arrangement on or around the sensor.

38. The method in accordance with claim 37, further comprising enabling the sensor to utilize a second nanostructure, further comprising enabling the first nanostructure and the second nanostructure to be electrically coupled in series between the first and second electrodes.

39. The method in accordance with claim 38, wherein the detecting further comprises a function of electrical characteristics of the first and second nano structures.

40. The method in accordance with claim 26, further comprising exposing the first nanostructure to the object directly or through a carrier, wherein the carrier comprises a solution, a liquid, a gas, or a carrier particle.

41. The method in accordance with claim 40, further comprising exposing the first nanostructure the object via a change in a concentration of the object or via a change in a concentration the carrier of the object.

42. The method in accordance with claim 26, further comprising varying the electrical characteristic of the first nanostructure when the first nanostructure is exposed to the electromagnetic radiation.

43. The method in accordance with claim 26, further comprising selectively varying the electrical characteristic of the first nanostructure based on a property of the object or a carrier of the object.

44. The method in accordance with claim 26, further comprising configuring the first and second electrodes to be arranged as concentric electrodes.

45. The method in accordance with claim 26, further comprising operating the sensor as a variable resistance sensor, and wherein the first nanostructure is capacitively coupled with the object or a carrier of the object.

46. The method in accordance with claim 26, further comprising operating the first nanostructure as an electrical switch or an electrical gate between the first and second electrodes when exposed to the object to be sensed.

* * * * *

UNITED STATES PATENT AND TRADEMARK OFFICE
CERTIFICATE OF CORRECTION

PATENT NO.         : 8,072,226 B2
APPLICATION NO.    : 11/995916
DATED              : December 6, 2011
INVENTOR(S)        : Young June Park Page 1 of 1

It is certified that error appears in the above-identified patent and that said Letters Patent is hereby corrected as shown below:

IN THE CLAIMS:

In column 15, line 24, claim 19, delete "(metal" and insert -- metal --, therefor.

In column 15, line 40, claim 24, delete "claim 12," and insert -- claim 16, --, therefor.

In column 16, line 51, claim 39, delete "nano structures." and insert -- nanostructures. --, therefor.

In column 16, line 57, claim 41, after "nanostructure" insert -- to --.

In column 16, line 59, claim 41, after "concentration" insert -- of --.

Signed and Sealed this
Twenty-first Day of February, 2012

David J. Kappos
*Director of the United States Patent and Trademark Office*